United States Patent [19]

Venkateswaran

[11] Patent Number: 5,549,888
[45] Date of Patent: Aug. 27, 1996

[54] AQUEOUS TOPICAL ANTI-ACNE COMPOSITIONS OF LOW PH

[75] Inventor: Ananthanarayan Venkateswaran, Kobe, Japan

[73] Assignee: Procter & Gamble, Cincinnati, Ohio

[21] Appl. No.: 189,364

[22] Filed: Jan. 31, 1994

[51] Int. Cl.$^6$ .......................... A61K 31/74; A61K 31/60
[52] U.S. Cl. ........................ 424/78.02; 514/859
[58] Field of Search ................... 514/859; 424/78.02

[56] References Cited

U.S. PATENT DOCUMENTS

| | | | |
|---|---|---|---|
| 3,821,370 | 6/1974 | Tenta | 424/145 |
| 4,318,907 | 5/1982 | Kligman et al. | 424/230 |
| 4,542,129 | 9/1985 | Orentreich | 514/178 |
| 4,720,353 | 1/1988 | Bell | 252/309 |
| 4,767,750 | 8/1988 | Jacquet et al. | 514/157 |
| 4,800,197 | 1/1989 | Kowez et al. | 514/162 |
| 4,891,227 | 1/1990 | Thaman et al. | 424/443 |
| 4,891,228 | 1/1990 | Thaman et al. | 424/443 |
| 5,036,077 | 7/1991 | Van Broeck et al. | 514/317 |
| 5,262,407 | 11/1993 | Tereque et al. | 514/159 |

FOREIGN PATENT DOCUMENTS

H3-279318A 12/1991 Japan .

OTHER PUBLICATIONS

International Journal of Pharmaceuticals, 74 (1991)229–236, titled "Aspects of the transdermal delivery of prostaglandins".

*Primary Examiner*—Peter F. Kulkosky
*Attorney, Agent, or Firm*—Anthony D. Sabatelli; David K. Dabbiere

[57] ABSTRACT

An aqueous topical composition with low pH comprising an acidic anti-acne agent and a water soluble glycol ether. The composition is useful for exfoliation and prevention or treatment of acne. In one preferred embodiment of the present invention, the composition further comprises a nonionic surfactant and a silicone copolymer.

1 Claim, No Drawings

AQUEOUS TOPICAL ANTI-ACNE COMPOSITIONS OF LOW PH

TECHNICAL FIELD

The present invention relates to an aqueous topical composition such as lotions, toners, and astringents comprising an acidic anti-acne agent and a water soluble glycol ether which is useful for exfoliation and prevention or treatment of acne.

BACKGROUND

The natural process of aging and the environment can lead to damage of the skin, affecting both its structure and functions. The skin keeps its condition through an inherent cycle of renewal, or natural exfoliation, that causes older, surface cells to drop off and allows fresher, newer skin to rise to the surface.

Acne is a follicular dermatosis. The comedo, which is the initial lesion of acne, resulting from the impaction of horny cells with the sebaceous follicle, develops in several stages. Primarily comedones develop first as microcomedones where the follicular ostium begins to be distended by horny material to form keratin plugs. The first visible lesion is the closed comedo or whitehead. Dilation of the follicular ostium by dark pigmented horny material marks the onset of an open comedo or blackhead. Subsequent rupture of closed or open comedones results in formation of secondary comedones which are generally larger and more irregularly shaped.

The bricks of the horny framework of comedones are corneocytes (i.e. individual dead skin cells) which are held together by a cement-like substance of extracellular lipids. Closed and open comedones develop into the nodules and pustules identified with inflammatory acne. Although there are multiple factors that appear to be operative in the pathogenesis of acne, it is the formation of keratin plugs that is the common denominator.

It is therefore apparent that a treatment directed at preventing or dissolving such keratin plugs (keratolysis) would reduce the compaction necessary to produce the comedo as well as helping to unseat existing comedones (comedolysis).

Acidic anti-acne agents are believed to cause a reduction in intercellular cohesion of the corneocytes, thereby dissolving the existing keratin plugs as well as preventing the formation of new ones. In order to best exert its keratolytic and comedolytic effect, it is desirable to deliver and deposit optimal concentrations of acidic anti-acne agents in the stratum corneum. Delivery of anti-acne agents through an aqueous system is beneficial for this purpose.

Acidic anti-acne agents are also believed to enhance the natural exfoliation process of the normal skin at relatively lower concentrations. It has been suggested that an appropriate cycle of efficient exfoliation helps the skin look and feel smoother, and reduces fine dry lines and provide even skin tone. Such refreshing feel of the skin is generally associated with an aqueous product. Thus, it is beneficial to combine the exfoliation benefit with refreshing feel attributed to an aqueous product.

However, most of these anti-acne agents are virtually insoluble in water, and thus difficult to incorporate these into aqueous systems. Furthermore, acidic anti-acne agents are most effective at low pH when a high concentration of free acid is present. It would thus be desirable to deliver the agent from an aqueous system at a low pH, at which the agent exists significantly in protonated form. This is particularly true for salicylic acid which is a well recognized anti-acne agent. Conventionally, high levels of alcohol and surfactants have been used to solubilize anti-acne agents. High levels of alcohol and surfactant can lead to compositions which are irritating when applied topically to the skin.

Consequently, it would be desirable to deliver acidic anti-acne agents in soluble form through a mild, yet refreshing aqueous system.

OBJECT OF THE INVENTION

It is an object of the present invention to provide an aqueous topical composition which is useful for exfoliation and prevention or treatment of acne.

It is also an object of the present invention to provide an aqueous topical composition which causes less irritation and dryness to the skin.

It is further an object of the present invention to provide an aqueous topical composition which gives light moisturizing and smooth touch to the skin.

It is further an object of the present invention to provide an aqueous topical composition which gives refreshing, non-sticky touch to the skin.

It is further an object of the present invention to provide an aqueous topical composition which has a clear appearance.

SUMMARY OF THE INVENTION

The present invention relates to an aqueous topical composition useful for exfoliation and prevention or treatment of acne comprising an acidic anti-acne agent and a water soluble glycol ether; wherein said composition has a pH of about 2.5–4.0.

DETAIL DESCRIPTION OF THE INVENTION

All percentages and ratios are based on weight, and all measurements are conducted at 25° C., unless otherwise specified.

ANTI-ACNE AGENT

A first essential component of the present invention is an acidic anti-acne agent. An acidic anti-acne agent of the present invention is an active ingredient which is most effective in its protonated form. The protonated form is taken at a pH of typically 2.5–4.0. Nonlimiting examples of anti-acne agents useful in the present invention are salicylic acid, retinoic acid, azelaic acid, lactic acid, glycolic acid, pyruvic acid, flavonoids and its derivatives, and mixtures thereof. The preferred anti-acne agent used in the composition herein is salicylic acid.

The anti-acne agent is comprised at a safe and effective level for topical application. Typically, the anti-acne agent is comprised at a level of 0.1%–10%. When comprised in compositions for cosmetic use, the anti-acne agent is comprised at a level of 0.1%–2%, more preferably 0.1%–1.5%, most preferably 0.5–1.5%.

WATER SOLUBLE GLYCOL ETHER

The second essential component of the present invention is a water soluble glycol ether agent. Glycol ether useful in the present invention is a water soluble glycol ether. Water soluble glycol ether acts as a solubilizer of acidic anti-acne agent, and also as a humectant which provides light moisturizing effect to the skin. The compositions of the present invention comprise an amount of water soluble glycol ether which can solubilize the acidic anti-acne active in the composition. Typically, the compositions of the present invention comprise 5%–20%, preferably 5–15%, most preferably 10–12.5% of water soluble glycol ether.

Water soluble glycol ether can be characterized by the general formula: $R^1$—O—$[(CH_2)_mO]_nH$; wherein $R^1$ is an alkyl of 1 to 6 carbon atoms, m is from about 2 to about 3, and n is from about 1 to about 2. Examples of the alkylene/ dialkylene group include ethylene, propylene and diethylene groups. Examples of the alkyl group $R^1$ include methyl, ethyl, propyl, butyl, hexyl groups. This glycol ether having a diethylene group as the alkylene group and ethyl group as the alkyl moiety is diethyleneglycol monoethyl ether which has been given the CTFA designation ethoxydiglycol. One of the most preferred is commercially available by the tradename Transcutol from Gattefosse, France.

Without being bound by theory, it is believed that the water soluble glycol ether used herein has an important effect on the thermodynamic activity of the anti-acne agent, particularly on solubility.

NONIONIC SURFACTANT

Compositions of this invention can optionally comprise 1–5%, preferably 2% of a nonionic surfactant. The nonionic surfactant acts as a co-solubilizer of anti-acne agents, thereby allowing higher agent level when using the same solvent. Nonionic surfactants useful herein include any of the well-known nonionic surfactants that have an HLB from about 10 to about 18, preferably from about 12 to 16.

Non-limiting examples of these nonionic surfactants are ethoxylated or propoxylated, preferably ethoxylated, alcohols and alkyl phenols with alcohol derivatives preferred. In general, these alcohol derivatives contain a straight or branched chain alkyl group having 8–22 carbons, preferably 10–20 carbons, more preferably 12–20 carbons, and generally contain from about 6 to about 30, preferably from about 8 to about 25, ethylene oxide or propylene oxide groups. Among these ethoxylated and propoxylated alcohols, the ethoxylated derivatives are preferred.

Preferred for use herein are polyethylene oxide ethers derived from lauryl alcohol, cetyl alcohol, oleyl alcohol, stearyl alcohol, isocetyl or isostearyl alcohol and mixtures thereof. Most preferred for use herein is isocetyl ether condensed with an average of 20 moles of ethyleneoxide, known by CTFA designation as Isoceteth 20.

COPOLYMER

Compositions of this invention can optionally comprise a dialkylpolysiloxane-polyoxyalkylene copolymer. Such copolymer is expected to improve the overall skin feel imparted by the composition and to reduce any irritation which can be caused by a component of the present invention. The composition preferably comprises 1–5% of dialkylpolysiloxane-polyoxyalkylene copolymer, most preferably 2–4% dialkylpolysiloxane-polyoxyalkylene copolymer.

Dialkylpolysiloxane-polyoxyalkylene copolymer useful herein include those which are soluble in water. Dimethylpolysiloxane-polyoxyalkylene copolymers, known as Dimethicone copolyols where the polyoxyalkylene group can be a polyoxyethylene or a polyoxypropylene group or a combination of both, are particularly useful. The dimethylpolysiloxane portion is typically made of from 10 to about 30 units, preferably around 15 to 20 units. The polyalkylene portion is typically made of from 8 to about 12, preferably from 10 to about 12 units.

SOLVENT

Solvents used in the present invention are selected depending on variables such as the remainder components, viscosity, product appearance, and desired skin-feel characteristic of the composition.

The primary solvent is water. The solvent may consist essentially of water.

Non-limiting examples of other optional solvents useful in the present invention are lower alcohols having 1 to 3 carbons such as ethanol and isopropanol, and polyhydric alcohols such as propylene glycol, hexylene glycol, glycerin, and propane diol.

Ethanol is preferably comprised upon making compositions which are designed to impart a refreshing feel or cool sensation to the skin. It is known that ethanol in the composition helps improve solubility of the anti-acne agent. Compositions of this invention can comprise 5–15% ethanol, most preferably 8–12% ethanol. This level of ethanol is expected to provide the desired refreshing feel to skin without being irritating or excessively drying to the skin.

OTHER OPTIONAL COMPONENTS

Other optional components can be included in the aqueous topical compositions of the present invention, depending on the needs of the product. Non-limiting examples of such optional components include additional surfactants, ultraviolet and infrared screening and absorbing agents, skin conditioning agents, perfume, color, pH adjusters, dyes, vitamins, proteins, plant extracts, and nutrients.

A wide variety of acids, bases, buffers, and sequestrants can be utilized to adjust and/or maintain the pH and ionic strength of the compositions useful in the present invention. Materials useful for adjusting and/or maintaining the pH and/or the ionic strength include sodium carbonate, sodium hydroxide, hydrochloric acid, phosphoric acid, sulfuric acid, acetic acid, sodium acetate, sodium hydrogen phosphate, sodium dihydrogen phosphate, citric acid, sodium citrate, sodium bicarbonate, triethanolamine, EDTA, disodium EDTA, tetrasodium EDTA, and the like.

EXAMPLES

The following examples illustrate the compositions of the present invention, but are not intended to be limiting thereof. All percentages and ratios are based on weight, and all measurements are conducted at 25° C. unless otherwise specified.

TABLE 1

| COMPONENT | AMOUNT (% W/W) |
|---|---|
| Salicylic acid | 1.5 |
| Transcutol* | 10.0 |
| Isoceteth | 4.0 |
| Dimethicone copolyol | 4.0 |
| Purified water | qs to 100 |
| Ethanol | 10.0 |
| Propylene glycol | 2.5 |
| Glycerin | 0.5 |
| Sodium citrate | 0.15 |
| Tetra sodium EDTA | 0.03 |

*Transcutol available from Gattefosse, France.

The components shown in TABLE 1 can be prepared by any conventional method well known in the art. A suitable method is as follows:

Salicylic acid and portion of Transcutol are combined and heated to about 70°–75° C. using a mixer at a rpm of about 150 to 200. Separately, a water phase is prepared consisting of remaining Transcutol, propylene glycol, glycerin, sodium citrate, tetra sodium EDTA, dimethicone copolyol and purified water. This water phase is also mixed using a mixer at 150 to 200 rpm at 70°–75° C. The salicylic acid/Transcutol mixture is then slowly added to the water phase and mixed at 75° C. for 30 minutes. The mixture is cooled to 45° C. and then ethanol is added. The obtained composition is a clear solution having a pH of about 2.8.

We claim:

1. An aqueous topical composition comprising by weight:
   (a) 0.1–2% of an acidic anti-acne agent selected from the group consisting of salicylic acid, retinoic acid, azelaic acid, lactic acid, glycolic acid, pyruvic acid, flavonoids and its derivatives, and mixtures thereof;
   (b) 5–20% of a water soluble glycol ether selected from the group consisting of the general formula: $R^1$—O—[$(CH_2)_mO]_nH$; wherein $R^1$ is an alkyl of 1 to 6 carbon atoms, m is from about 2 to about 3, and n is from about 1 to about 2; and mixtures thereof;
   (c) 1–5% of a nonionic surfactant having an HLB from about 10 to 18;
   (d) 1–5% of a water soluble dialkylpolysiloxane-polyoxyalkylene copolymer; and
   (e) 5–15% of a lower alcohol selected from the group consisting of monoalcohols having 1 to 3 carbons and mixtures thereof;
   wherein said composition has a pH of about 2.5–4.

* * * * *

UNITED STATES PATENT AND TRADEMARK OFFICE
CERTIFICATE OF CORRECTION

PATENT NO. : 5,549,888

DATED : August 27, 1996

INVENTOR(S) : Ananthanarayan Venkateswaran

It is certified that error appears in the above-identified patent and that said Letters Patent is hereby corrected as shown below:

At Column 2, line 62 "glycol ether agent." should read --glycol ether.--.

At Column 3, line 23 "preferably 2%" should read --preferably 2% - 4%--.

At Column 6, line 9 "(c)" should read --(e)--.

Signed and Sealed this

Tenth Day of December, 1996

Attest:

BRUCE LEHMAN

*Attesting Officer*  *Commissioner of Patents and Trademarks*